(12) United States Patent
Kubota et al.

(10) Patent No.: US 7,585,275 B2
(45) Date of Patent: Sep. 8, 2009

(54) CAPSULE ENDOSCOPE

(75) Inventors: Yukio Kubota, Saitama (JP); Takanobu Shiokawa, Kanagawa (JP); Toru Chiba, Tokyo (JP); Takaomi Sekiya, Tokyo (JP)

(73) Assignee: Hoya Corporation, Tokyo (JP)

( * ) Notice: Subject to any disclaimer, the term of this patent is extended or adjusted under 35 U.S.C. 154(b) by 493 days.

(21) Appl. No.: 11/332,202

(22) Filed: Jan. 17, 2006

(65) Prior Publication Data

US 2006/0170328 A1 Aug. 3, 2006

(30) Foreign Application Priority Data

Jan. 18, 2005 (JP) ............................ P2005-010137
Mar. 18, 2005 (JP) ............................ P2005-078843

(51) Int. Cl.
*A61B 1/06* (2006.01)
(52) U.S. Cl. ........................ 600/160; 600/178; 600/179
(58) Field of Classification Search ................. 600/109, 600/118, 121, 122, 129, 160, 171, 176, 178, 600/179, 476; 362/574
See application file for complete search history.

(56) References Cited

U.S. PATENT DOCUMENTS

| | | | |
|---|---|---|---|
| 4,439,197 A | | 3/1984 | Honda et al. |
| 5,167,626 A | | 12/1992 | Casper et al. |
| 5,840,014 A | * | 11/1998 | Miyano et al. ............... 600/125 |
| 5,951,464 A | * | 9/1999 | Takahashi et al. ........... 600/176 |
| 6,632,216 B2 | | 10/2003 | Houzego et al. |
| 6,855,111 B2 | | 2/2005 | Yokoi et al. |
| 7,001,329 B2 | | 2/2006 | Kobayashi et al. |
| 2003/0171652 A1 | * | 9/2003 | Yokoi et al. ................. 600/160 |
| 2005/0020880 A1 | * | 1/2005 | Miyake et al. ............... 600/121 |
| 2005/0049462 A1 | | 3/2005 | Kanazawa |
| 2005/0124858 A1 | * | 6/2005 | Matsuzawa et al. .......... 600/176 |
| 2005/0137459 A1 | * | 6/2005 | Chin et al. ................... 600/179 |
| 2005/0143624 A1 | * | 6/2005 | Iddan .......................... 600/112 |

FOREIGN PATENT DOCUMENTS

| | | |
|---|---|---|
| JP | 3-136636 | 6/1991 |
| JP | 6-114037 | 4/1994 |
| JP | 08146307 A * | 6/1996 |
| JP | 2001-224552 | 8/2001 |
| JP | 2003-260025 | 9/2003 |
| JP | 2004357933 A * | 12/2004 |

OTHER PUBLICATIONS

English Language Abstract of JP 3-136636.

(Continued)

*Primary Examiner*—John P Leubecker
*Assistant Examiner*—Samuel Candler
(74) *Attorney, Agent, or Firm*—Greenblum & Bernstein, P.L.C.

(57) ABSTRACT

A capsule endoscope has an outer cover including a transparent cover, a surface light emitting device, and a photographing optical system. The outer cover seals an inside space of the capsule endoscope. The light emitting device, which is disposed in the inside space of the capsule endoscope, emits light to an object through the transparent cover. The photographing optical system, which is disposed opposite to the transparent cover in the inside space, captures light reflected from the object which passes through the transparent cover.

6 Claims, 13 Drawing Sheets

OTHER PUBLICATIONS

English Language Abstract of JP 6-114037.
English Language Abstract of JP 2001-224552.
English Language Abstract of JP 2003-260025.
P. Swain, *Wireless Capsule Endoscopy*, Gut, vol. 52 (Suppl. IV), 2003.

Leung et al., *Wireless Capsule Endoscopy in Chinese Patients with Suspected Small Bowel Diseases*, Hong Kong Med J. vol. 10, 2004, pp. 179-183.

* cited by examiner

CAPSULE ENDOSCOPE

BACKGROUND OF THE INVENTION

1. Field of the Invention

The present invention relates to a capsule endoscope having a light emitting device and a photographing optical system therein.

2. Description of the Related Art

Conventionally, a capsule endoscope is used in medical and industrial fields. When it is used in the medical field, the capsule endoscope is swallowed so as to enter the body of a patient, and it photographs images inside the body. The photographed images are transmitted as signal out of the body by radio, so that a doctor can observe the inside of the body. The capsule endoscope doesn't have an insertion member like a conventional endoscope, and this means pain is eliminated for the patient.

Generally, the capsule endoscope comprises a cylindrical cover and two dome-shaped covers which cover both ends of the cylindrical cover. One of the dome-shaped covers is a transparent cover, and a light emitting device and a photographing optical system are disposed opposite to the transparent cover. The light emitting device emits light to illuminate an area inside the body through a transparent cover, and the photographing optical system captures an image of the illuminated area inside the body.

In this case, most of the light emitted by the light emitting device permeates through the transparent cover and is radiated inside the body. However, part of the light is reflected by the transparent cover, and the reflected light is input to the photographing optical system. Due to this, flares appear in the photographed image, which deteriorate the quality of the image. Therefore, it is known that the position of the entrance pupil of the photograph optical lens system should coincide with the center of curvature of the transparent cover to prevent the reflected light from entering to the photographing optical system, as shown in Japanese Unexamined Patent Publication (KOKAI) NO. 2003-260025.

However, even if the position of the entrance pupil is located as described above, it is difficult to prevent all the reflected light from entering the photographing optical system.

Further, conventionally, an inorganic LED (light-emitting diode) is used as the light emitting device. However, the illumination range of an inorganic LED is not so large, so several inorganic LEDs have to be provided in the capsule endoscope to obtain a sufficient illumination range. In this case, the inorganic LEDs are arranged around the imaging device, so that other components can not be arranged around the imaging device and it is difficult to miniaturize the capsule endoscope.

SUMMARY OF THE INVENTION

Therefore, an object of the present invention is to provide a capsule endoscope which can be miniaturized. Another object of the present invention is to provide a capsule endoscope which can prevent the reflected light by a transparent cover from entering the photographing optical system.

According to the present invention, there is provided a capsule endoscope having an outer cover that seals an inside space of the capsule endoscope, the outer cover including a transparent cover. The capsule endoscope comprises a surface light emitting device (plane emission device, surface emitting device), and a photographing optical system. The surface light emitting device that is disposed in the inside space, emits light to an object through the transparent cover. The photographing optical system that is disposed opposite to the transparent cover in the inside space, captures light reflected from the object, which passes through the transparent cover.

The surface light emitting device is preferably disposed on an inner surface of the transparent cover. More preferably, the surface light emitting device extends along the inner surface.

For example, the outer cover is a cylindrical cover having an end which is said transparent cover being dome-shaped. The transparent cover preferably includes a hemisphere portion. More preferably, the surface light emitting device extends along the inner surface of the transparent cover other than that for a tip of the transparent cover and a circumference portion around the tip.

Optionally, the inner surface has a vertical surface that is vertical to an optical axis of the photographing optical system. In this case, the surface light emitting device extends along the vertical surface for example. The inner surface preferably has a plurality of the vertical surfaces. The surface light emitting device is disposed on each of the vertical surfaces, and each surface light emitting device extends coaxially around the optical axis.

Preferably, the surface light emitting device is disposed on an inner surface of said transparent cover other than that for a field of vision of the optical system. For example, the surface light emitting device is ring-shaped and is located around an optical axis of the photographing optical system. The surface light emitting device is an organic electroluminescent device, for example.

According to the present invention, there is provided a capsule endoscope having an outer cover that seals an inside space of the capsule endoscope, the outer cover including a transparent cover. The capsule endoscope comprises a photographing optical system, and a light emitting device. The photographing optical system is disposed opposite to the transparent cover in the inside space, and captures light, which is reflected from an object, located in front of the optical system, and which has passed through the transparent cover. The optical system includes at least one optical element. The light emitting device that is disposed in the inside space emits light to illuminate the object, through the transparent cover. The optical element that is disposed at the most forward position in the optical system is adjacent to the transparent cover. Further, the optical element can mean a lens or an imaging device.

The photographing optical system is preferably provided on the transparent cover. More preferably, the photographing optical system is held on the transparent cover through a holder which is provided on the transparent cover. The holder includes a cylindrical portion having an end opening which is bonded to the transparent cover for example.

Optionally, a part of the transparent cover is formed as a positive or negative lens, of which an optical axis coincides with an optical axis of the optical system. The outer cover is a cylindrical cover having an end which is a transparent cover being dome-shaped, for example. Optionally, the transparent cover includes a hemisphere portion. Preferably, the light emitting device is disposed on an inner surface of the transparent cover. The light emitting device is preferably a surface light emitting device, and more preferably is an organic electroluminescent device. The surface light emitting device extends along an inner surface of the transparent cover for example.

BRIEF DESCRIPTION OF THE DRAWINGS

The objects and advantages of the present invention will be better understood from the following description, with reference to the accompanying drawings in which.

DESCRIPTION OF THE PREFERRED EMBODIMENTS

The present invention will be described below with reference to the embodiments shown in the drawings.

Figure 1:
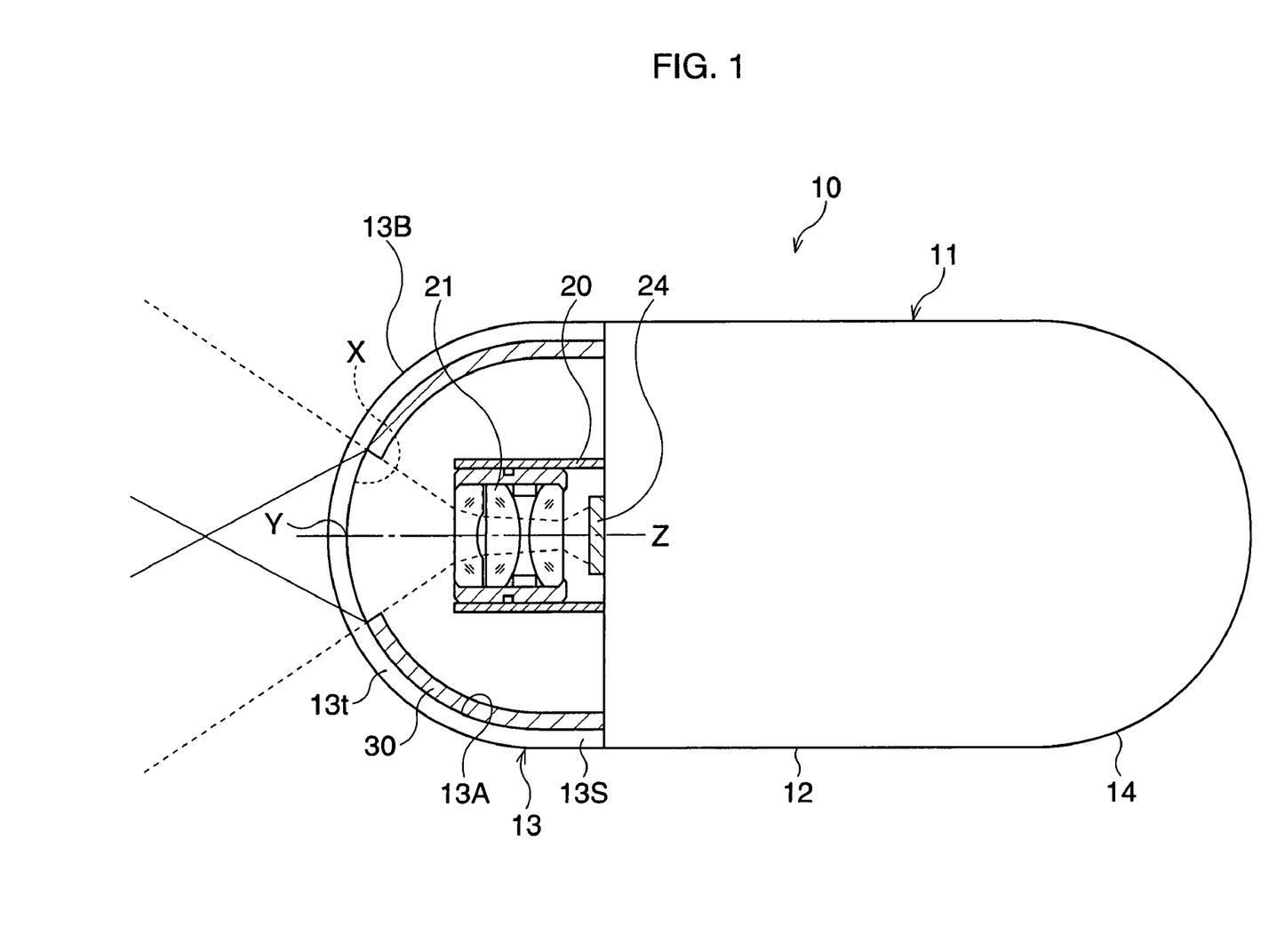
FIG. 1 is a side view, partly sectioned, of a capsule endoscope in the first embodiment of the present invention.
Figure 2:
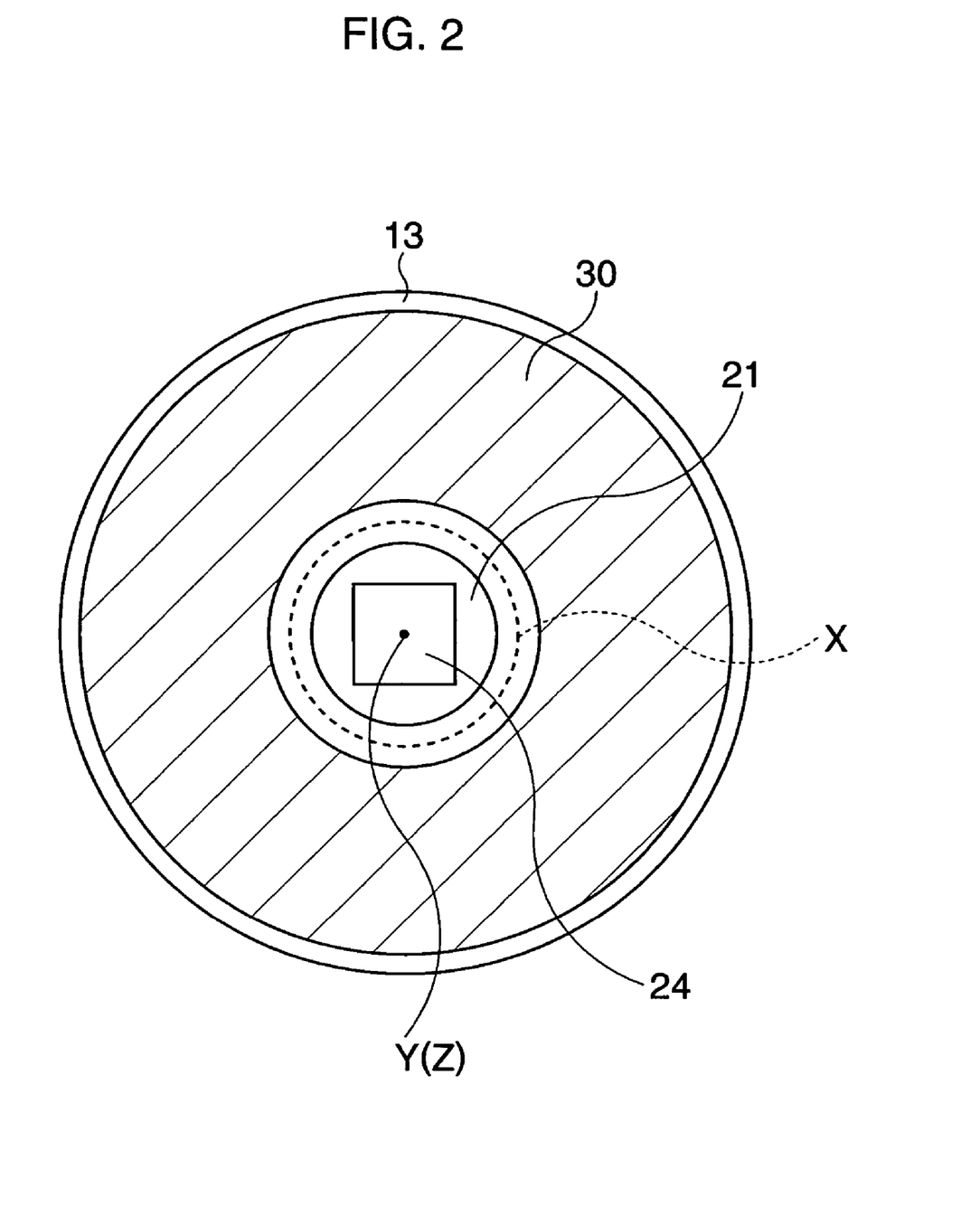
FIG. 2 is a front view of the capsule endoscope in the first embodiment.

FIGS. 1 and 2 show a capsule endoscope, to which a first embodiment of the present invention is applied. A capsule endoscope 10 has an outer cover 11, which seals an inside space of the capsule endoscope 10. The outer cover 11 includes a cylindrical cover section 12 which is opaque, a transparent cover section 13 which covers an end of the cylindrical cover section 12, and an opaque cover section 14 which covers another end of the cylindrical cover section 12. The transparent cover section 13 and the opaque cover section 14 are dome-shaped. A cylindrical frame is provided along the inner surface of the cylindrical cover section 12. The cylindrical frame holds a power supply unit, a circuit-board, an antenna, and so on (not shown in FIG. 1) which are disposed at the inside of the outer cover 11. The power supply unit has a battery, which supplies power to an organic electroluminescent device as described below. The circuit-board has an image processing circuit and a solid-state imaging device (e.g. CCD) 24 and so on thereon.

The transparent cover section 13 includes a cylindrical portion 13s which is connected to the end of the cylindrical cover section 12, and a hemisphere portion 13t having a hemispherical shape which gets approaches an optical axis Z (as described below) as it approaches a tip Y of the transparent cover section 13. The transparent cover section 13 is formed by the transparent material (e.g. resin).

An objective lens system 21 is disposed in the transparent cover section 13 and is opposite to an inner surface 13A of the transparent cover section 13. The objective lens system 21 is held by a lens holder frame 20, which is connected to the cylindrical frame (not shown in FIG. 1) which is disposed in the cylindrical cover section 12. The lens holder frame 20 having a cylindrical shape projects from the inside of the cylindrical cover section 12 into the transparent cover section 13. An optical axis Z of the objective lens system 21 passes through the center of the hemisphere portion 13t and the tip Y. The imaging device 24 is disposed behind to the objective lens system 21 and on the optical axis Z. The imaging device 24 and the objective lens system 21 form a photographing optical system. The field of vision X of the imaging device 24 becomes enlarged as it is moved forward, as shown in FIG. 1. The field of vision X is circular around the tip Y on an inner surface 13A of the transparent cover section 13 when viewed from the front as shown in FIG. 2. An inner surface 13A and an outer surface 13B of the transparent cover section 13 are parallel, so that the transparent cover section 13 does not have the lens power.

A surface light emitting device 30 which is an organic electroluminescent device (hereafter "EL device") is disposed on the inner surface 13A. The EL device 30 extends along almost all of the inner surface 13A other than that for the field of vision X. The EL device 30 (namely, the emitting is surface of the EL device) extends in a ring-shape, other than that for the tip Y and a circumference portion around the tip Y when viewed from the front as shown in FIG. 2. Namely, the EL device 30 is located around the optical axis Z.

Figure 3:
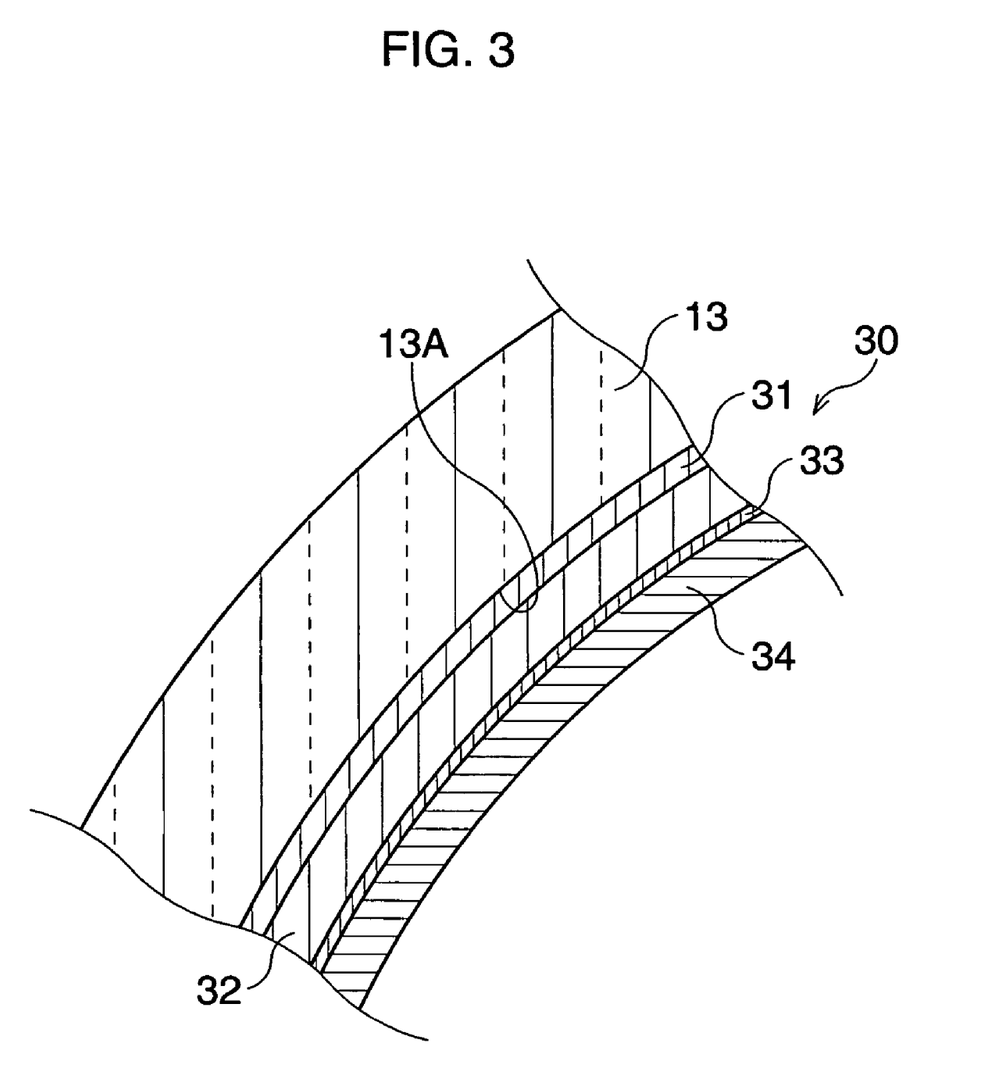
FIG. 3 is an enlarged sectional view of an organic electroluminescent device in the first embodiment.

FIG. 3 shows the EL device 30. The EL device 30 comprises an anode 31, an lamination layer 32 including an organic emitting layer, and a cathode 33 that are disposed on the inner surface 13A in sequence from the inner surface 13A as shown in FIG. 3, and a seal film 34 is provided on the cathode 33. The seal film 34 adheres to the circumference of the inner surface 13A so that the anode 31, the lamination layer 32 and, the cathode 33 are sealed by the seal film 34. The anode 31 and cathode 33 extend to the outside from the sealed inside, between the seal film 34 and the inner surface 13A, and are connected to the power supply unit.

The anode 31 is the transparent layer, which is formed of ITO (Indium Tin Oxide), ATO (antimony doped tindioxide), or ZnO (zinc oxide) for example. The cathode 33 may be a transparent layer which is formed of ITO, ATO, or ZnO, but is preferably an opaque or reflective layer (e.g. an aluminum layer), because this prevents the light emitted by the EL device 30 from entering the imaging device 24 through the cathode 33. The lamination layer 32 has in sequence from the anode 31 side, a hole-transporting layer, the organic emitting layer, an electron-transporting layer and so on, so that the lamination layer 32 can emit white light. The seal film 34 is formed of a metallic oxide, or nitride, for example. The electric current is input between the anode 31 and the cathode 33, thus the EL device 30 emits light to the outside of the capsule endoscope 10, which passes through the transparent cover section 13.

The layer-thickness direction of each layer in the EL device 30 to which the EL device 30 mainly emits the light inclines outward to the optical axis Z. However, the angle of the layer-thickness direction with the optical axis Z becomes smaller as the EL device 30 is closer to the tip Y. In addition to this, the emitted light by the EL device 30 is diffused light as shown in FIG. 1, so the EL device 30 also emits the light to the direction inclining to the layer-thickness direction. Therefore, the light emitted by a part of the EL device 30 which is close to the tip Y can be radiated to the field of vision X, and can be used as the direct illumination.

On the other hand, the light emitted by a part of the EL device 30 which is far from the tip Y can not be radiated to the field of vision X directly. However, it can be radiated to the surrounding part of the field of vision X, so it can be used as the indirect illumination, which results in illuminating the field of vision X. Due to this, all of the light emitted by the EL device 30 is used effectively.

The light emitted by the EL device 30 is reflected by an object inside the body, which is located in front of the objective lens system 21, and the reflected light is received on the imaging device 24 through the transparent cover section 13 and the objective lens system 21. At the imaging device 24, the image corresponding to the received light is formed, and is converted to image signals. The image signals are sent to the image processing circuit and are processed according to predetermined image processes therein so that they are converted to transmission signals. The transmission signals are transmitted from the antenna in the capsule endoscope 10 to an antenna which is located outside the body. The transmission signals are input to a display device from the antenna and are displayed thereon as the images.

In this embodiment, the EL device 30 (surface light emitting device) is used as a light emitting device and is disposed on the inner surface 13A of the transparent cover section 13. Due to this, a specific space where the light emitting device is disposed is not necessary, therefore the capsule endoscope 10 can be miniaturized. Further, the anode 31 is directly laminated on the inner surface 13A in this embodiment therefore the structure of the light emitting device 30 can be simple. In addition to this, the color rendering properties of the EL device 30 are better than those of an inorganic LED, so that the color representation in this embodiment is better than if an inorganic LED is used as the light emitting device.

Further, the EL device 30 can be arranged in the inside space of the capsule endoscope 10 except for on the inner surface 13A. For example, the EL device 30 which is plane ring-shaped can be arranged on the same plane where the imaging device 24 is disposed, and the EL device 30 can surround the imaging device 24. Similarly, the EL device 30 which is plane ring-shaped can be arranged on the same plane that the most forward lens of the objective lens system 21 is disposed on, and can surround it. Of course, the EL device 30 can be disposed between the plane where the most forward lens of the objective lens system 21 is disposed and the plane where the imaging device 24 is disposed.

However, if the EL device 30 is not disposed on the inner surface 13A, some of the light emitted by the EL device 30 is reflected by the inner surface 13A directly into the imaging device 21, so that flares appear on the image formed on the imaging device 21 and the quality of the image is deteriorated. Therefore, the EL device 30 is preferably disposed on the inner surface 13A in order to prevent the light emitted by the EL device 30 from reflecting from the inner surface 13A.

Furthermore, the objective lens system 21 can be omitted, and if so the transparent cover section 13 can have lens power so as to become the objective lens system.

Figure 4:
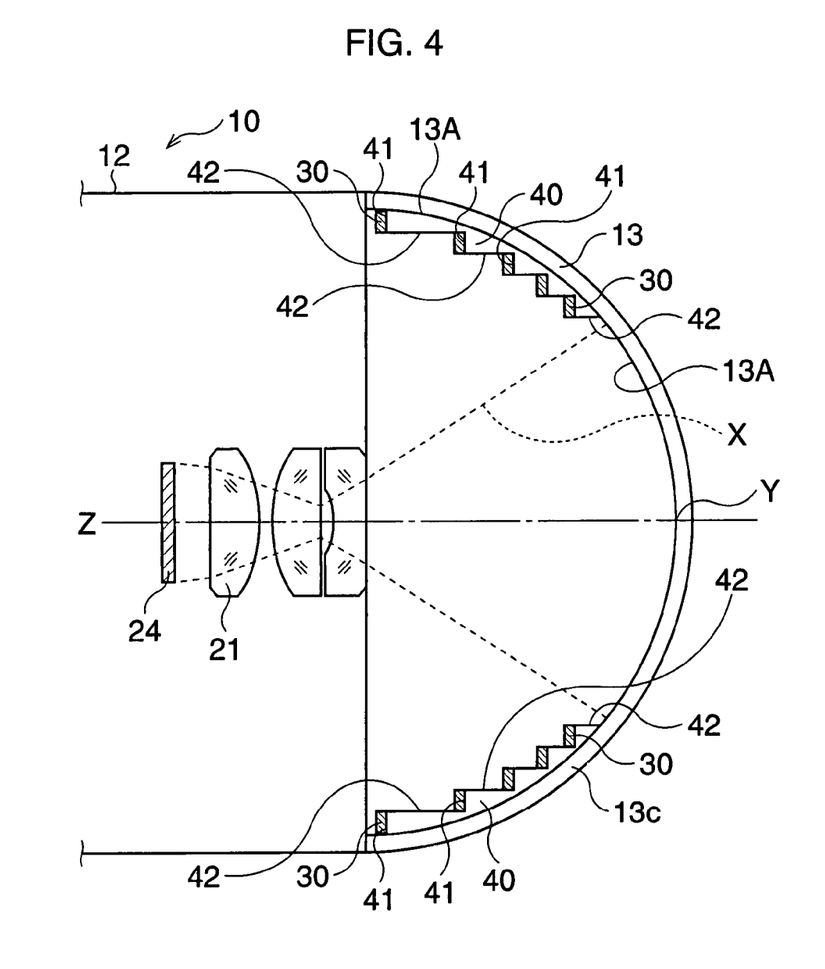
FIG. 4 is a side view, partly sectioned, of a capsule endoscope in the second embodiment of the present invention.
Figure 5:
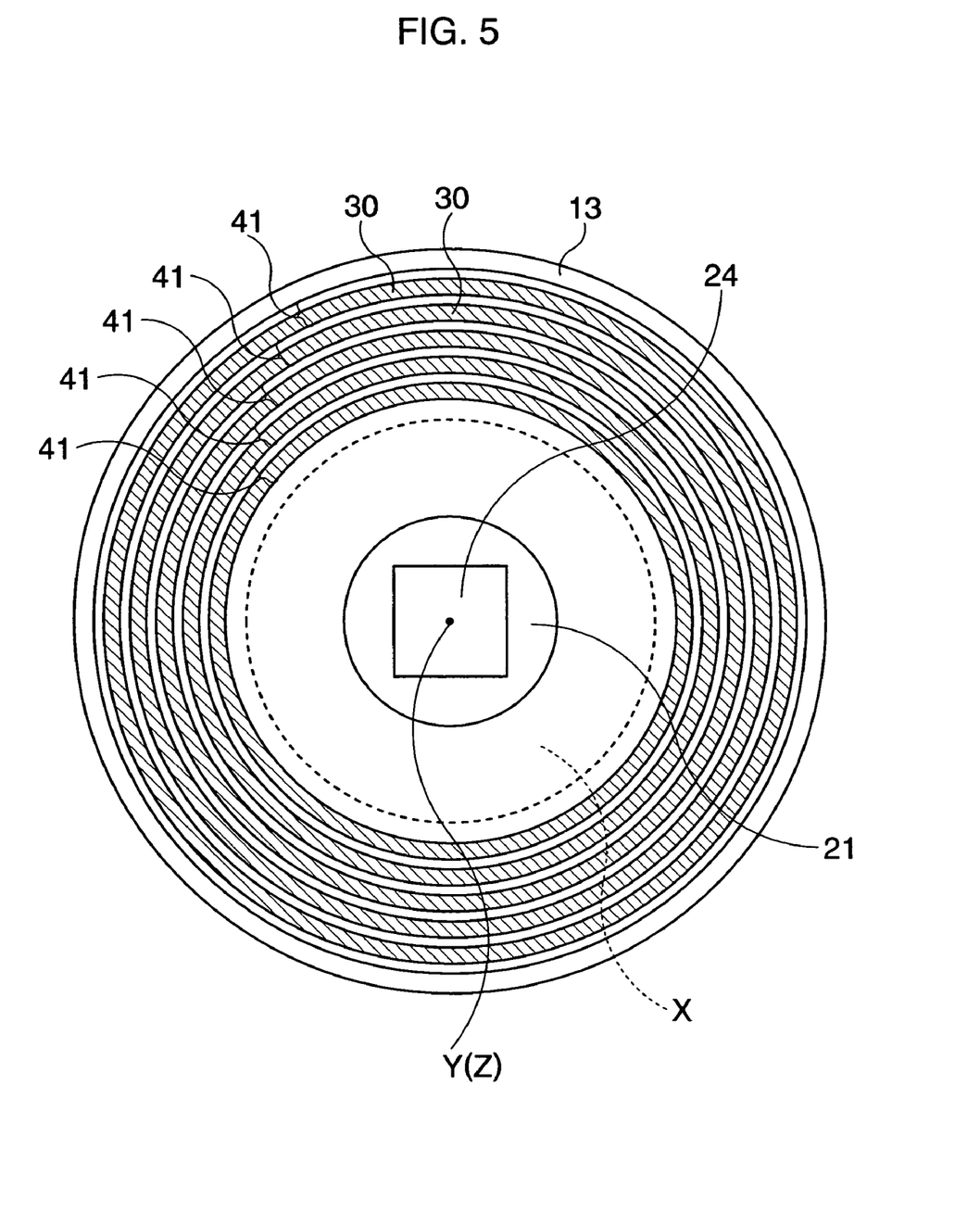
FIG. 5 is a front view of the capsule endoscope in the second embodiment.

The second embodiment of this invention will be explained using FIGS. 4 and 5. In this embodiment, the inner surface 13A has a plurality of vertical surfaces 41 which are vertical to the optical axis Z and which are arranged on the inner surface 13A other than that for the field of vision X. Each of the vertical surfaces 41 which are ring-shaped is coaxial around the optical axis Z, and is arranged apart from an inner side of the hemispherical surface of the inner surface 13A. Two adjacent vertical surfaces 41 are in contact with each other when viewed from the front as shown in FIG. 5, and are connected by the parallel surface 42 which is parallel to the optical axis Z as shown in FIG. 4. Due to these, the vertical surfaces 41 and the parallel surfaces 42 form a stair-shape when viewed from the side as shown in FIG. 4. The vertical surfaces 41 and the parallel surfaces 42 are formed on a substrate 40, which is bonded to the inner surface 13A.

The EL device 30 is disposed on each of the vertical surfaces 41. The EL device 30 comprises the anode which is laminated on the vertical surface 41, the lamination layer including the organic emitting layer which is laminated on the anode, and the cathode which is laminated on the lamination layer. The cathode is preferably a reflective layer which is formed of the aluminum for example. Due to this, some of the light emitted by the EL device 30 is reflected by the cathode and radiated to the outside of the capsule endoscope 10, so that the EL device 30 can illuminate the outside of the capsule endoscope 10 effectively. The seal film is covered over all of the cathodes of the EL devices 30 in order to seal the anode, the cathode, and the lamination layer. The cathodes and anodes are connected to the power supply unit so that the EL device 30 can be supplied with electric power.

The EL device 30 is formed by directly laminating the anode, the lamination layer, and the cathode in sequence on the vertical surface 41 in this embodiment. However, the EL device 30 can be formed as described below. Namely, the component is produced in advance by laminating the anode, the lamination layer, the cathode, and seal film in sequence on the ring-shaped substrate, and then the component can be adhered to the vertical surface 41.

Furthermore, the parallel surfaces 42 are preferably reflective surfaces. If so, some of the light emitted by the EL device 30 which is reflected at the parallel surfaces 42 radiates to the object, so that light emitted by the EL device 30 is effectively used as the illumination light.

In this embodiment, the layer-thickness direction coincides with the optical axis Z, so that the light emitted by the EL device 30 radiates to the field of vision X effectively.

In this embodiment, the transparent cover section 13 consists of the hemisphere portion 13*t*, but does not have the cylindrical portion 13*s*, because the substrate. 40 is preferably disposed on the inner surface 13A which approaches the optical axis Z as it approaches the tip Y.

Further, the vertical surfaces 41 are vertical to the optical axis Z in this embodiment, but may not be vertical to the optical axis Z. Similarly, the parallel surface 42 may not be parallel to the optical axis Z.

Figure 6:
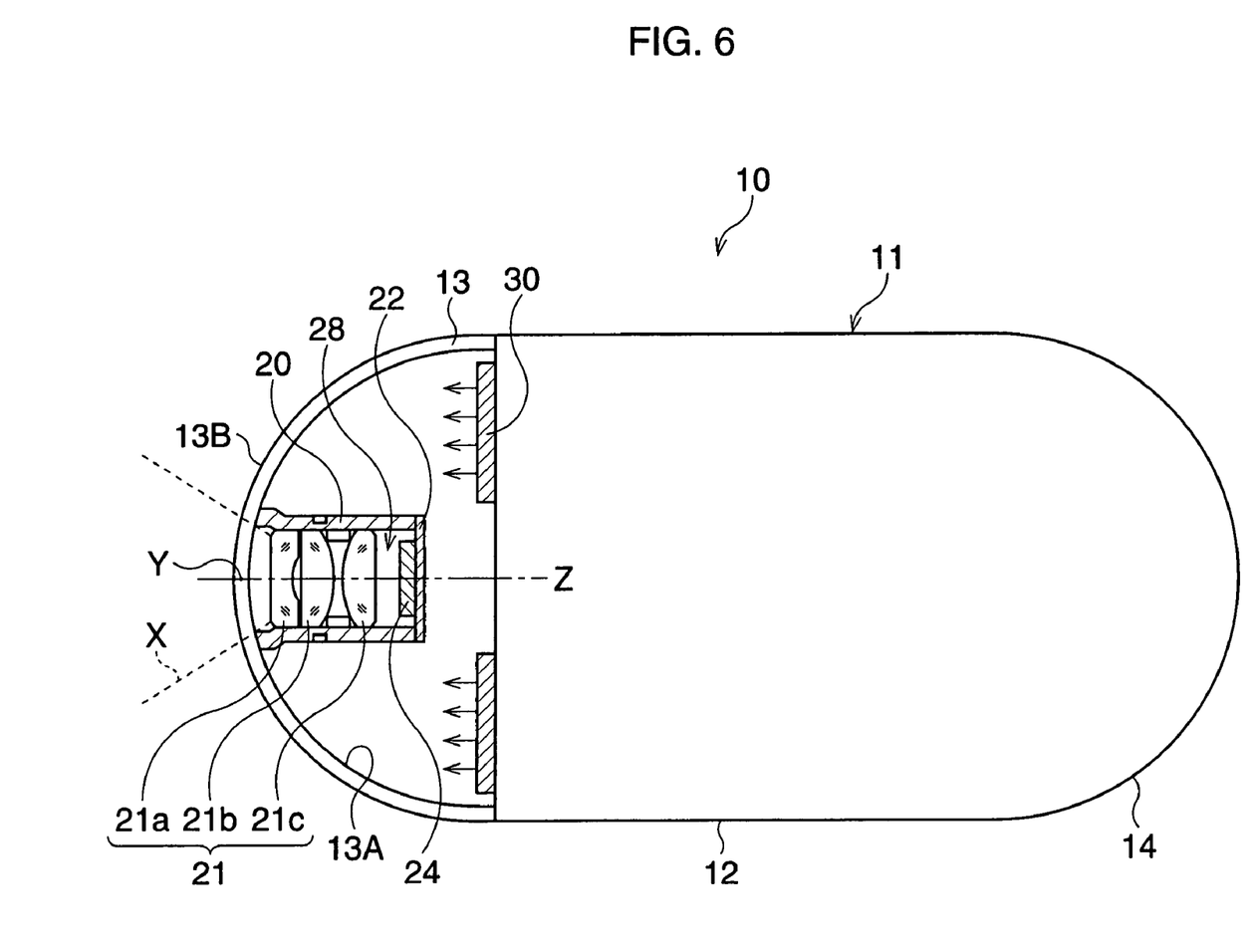
FIG. 6 is a side view, partly sectioned, of a capsule endoscope in the third embodiment of the present invention.

The endoscope 10 of the third embodiment in this invention will be explained using FIGS. 6 and 7, regarding the differences from the first embodiment.

In this embodiment, the transparent cover section 13 is hemisphere-shaped, similar to the second embodiment, and the lens holder frame 20 having a cylindrical-shape is disposed in the transparent cover section 13. The lens holder frame 20 is a cylinder in which one end of the cylinder is closed by a base portion 22, and another end thereof is an opening end which extends outward. The lens holder frame 20, which holds a photographing optical system 28, is provided on the inner surface 13A by bonding the opening end thereto. The photographing optical system 28 comprises the imaging device 24 and the objective lens system 21. The photographing optical system 28 receives light through the opening end of the lens holder frame 20. The optical axis Z of the objective lens system 21 coincides with the axis of the holder 28, the center of the transparent cover section 13, and the tip Y.

The objective lens system 21 comprises a negative lens 21a, a positive lens 21b, and a positive lens 21c in sequence from the transparent cover section 13 side. The negative lens 21a, which is disposed at the most forward position (namely, closet position to the object) in the objective lens system 21 on the optical axis Z, is adjacent to the inner surface 13A. The imaging device 24 is disposed on the base portion 22 behind to the objective lens system 21 on the optical axis Z. The imaging device 24 is connected to the image processing circuit in the cylindrical cover section 12 by a lead wire (not shown in FIG. 6) in order to send the image signal thereto.

Figure 7:
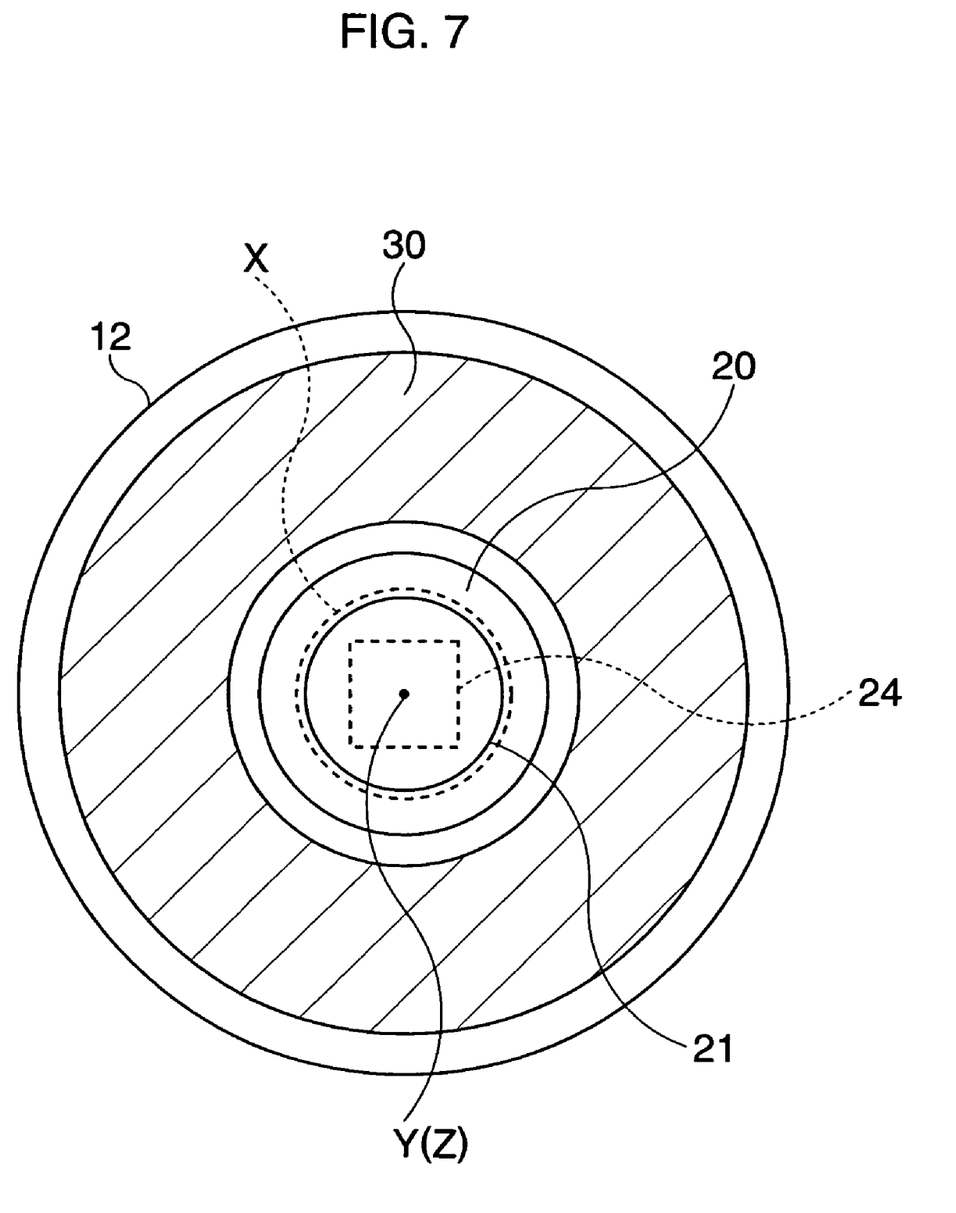
FIG. 7 is a front view of the capsule endoscope in the third embodiment.

The field of vision X is enlarged as the position of the field X gets further from the capsule endoscope 10, and is a circular around the tip Y on an inner surface 13A when viewed from the front as shown in FIG. 7, similar to the first embodiment. In this embodiment, the negative lens 21a which is disposed at the most forward position is adjacent to the inner surface 13A. Therefore, the diameter of the field of vision X at the inner surface 13A is substantially same as the diameter of the negative lens 21a. Namely, the diameter of the field of vision X in the inner surface 13A is smaller than the diameter of the opening end of the lens holder frame 20, so that the lens holder frame 20 does not shade the field of vision X.

The EL device 30 is disposed at a boundary plane between the cylindrical cover section 12 and the transparent cover section 13. Thus, the emitting surface of the EL device 30 extends along the plane vertical to the optical axis Z, so that the center of the luminous flux of the light emitted by the EL device 30 is parallel to the optical axis Z. The EL device 30 extends in a ring-shape and does not overlap the lens holder frame 20 in when viewed from the front as shown in FIG. 7, which prevents the light emitted by the EL device 30 from radiating to the lens holder frame 20.

Figure 8:
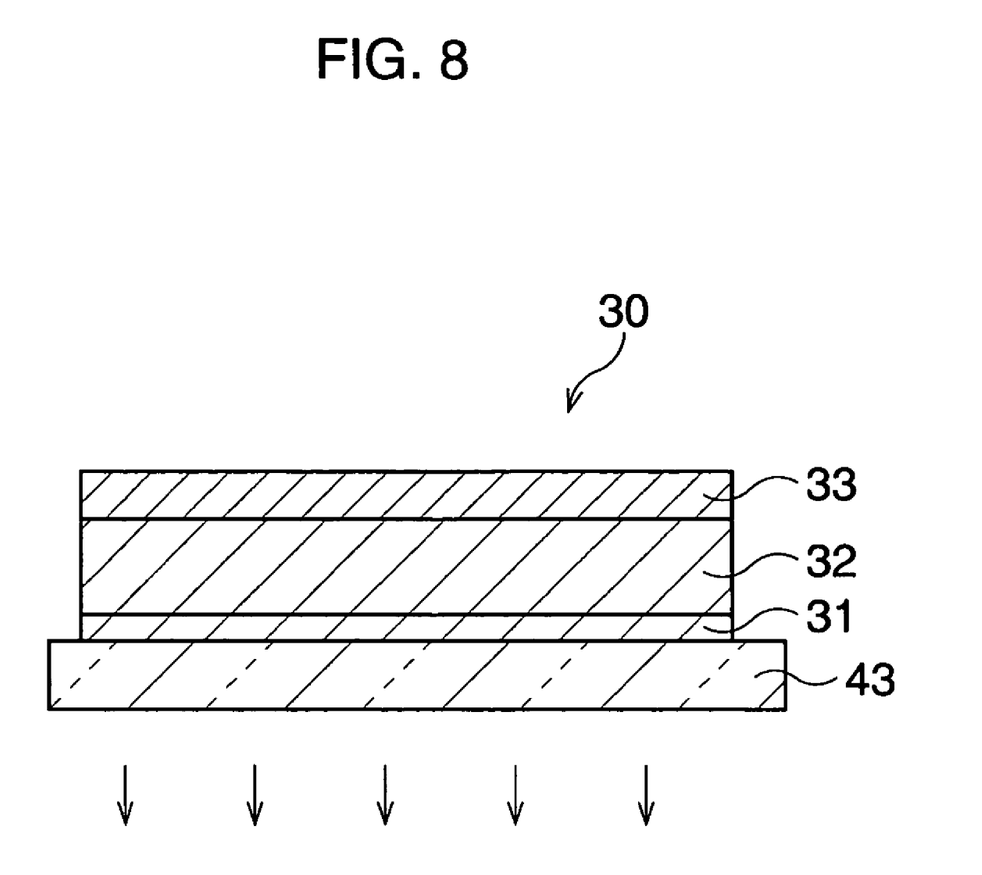
FIG. 8 is an enlarged sectional view of an organic electroluminescent device in the third embodiment.

FIG. 8 shows the EL device 30 in the third embodiment. The EL device 30 comprises the anode 31, the lamination layer 32, and the cathode 33 that are disposed on a substrate 43 in sequence from the substrate 43 as shown in FIG. 8, and the seal film (not shown in FIG. 8) is provided on the cathode 33. The anode 31, the lamination layer 32, the cathode 33, and the seal film have the same structure as in the first embodiment, therefore the explanations of these are omitted. Further, the EL device 30 is held by the cylindrical frame which is provided in the cylindrical cover, and the side of the substrate 43 in the EL device 30 is arranged at the front side in the capsule endoscope 10.

In this embodiment, the light emitted by the EL device 30 is refuse light therefore the emitted light radiates forward and enlarges the radiation area. Due to this, the emitted light radiates to a broad area inside the body inside (the object) and a part of the emitted light radiates to the lens holder frame 20 and the base portion 22. However, the emitted light is not input to the photographing optical system 28, because the lens holder frame 20 and the base portion 22 are opaque. Further the outer surfaces of the lens holder frame 20 and the base portion 22 can be reflective so as to reflect the emitted light.

In this embodiment, some of the light emitted by the EL device 30 permeates the transparent cover section 13 to radiate to the object but a part of the emitted light is reflected by the transparent cover section 13. However, the reflected light is not input to the imaging device 24 because the photographing optical system 28 is enclosed in the lens holder frame 20. Further, the negative lens 21a which is disposed at the most forward position in the photographing optical system 28 is adjacent to the inner surface 13A, therefore even if the photographing optical system 28 is not enclosed in the lens holder frame 20, almost all of the reflected light is not input to the photographing optical system 28.

Further, the photographing optical system 28 is disposed at the front of the boundary plane between the cylindrical cover section 12 and the transparent cover section 13 therefore the back space of the photographing optical system 28 can be utilized for other components, so that the capsule endoscope 10 can be miniaturized.

Figure 9:
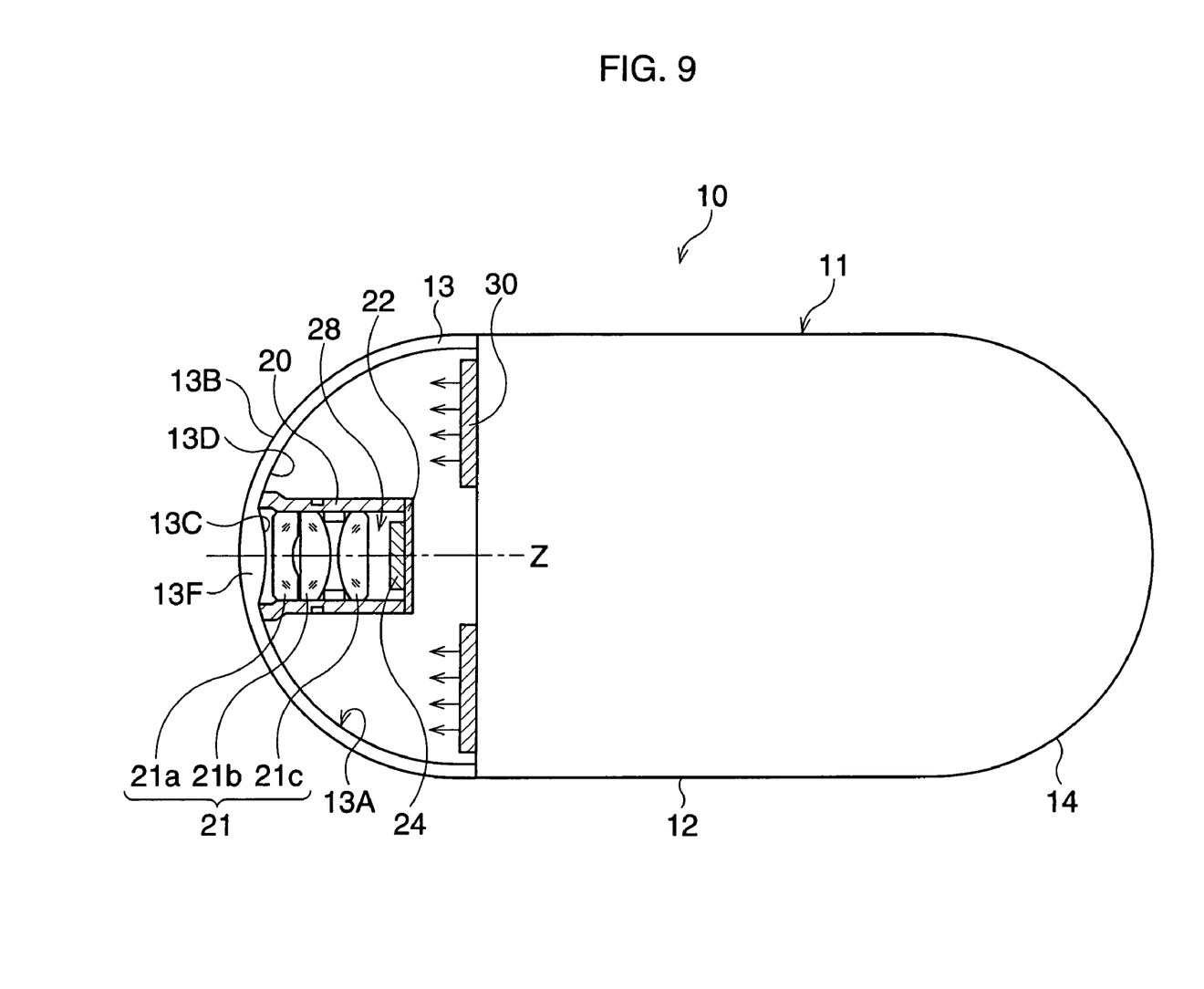
FIG. 9 is a side view, partly sectioned, of a capsule endoscope in the fourth embodiment of the present invention.

The FIG. 9 shows the capsule endoscope 10 of a fourth embodiment. The difference in this embodiment from the third embodiment is the structure of the inner surface 13A. Next, the difference from the third embodiment will be explained below.

In this embodiment, the inner surface 13A includes a first inner surface 13C which is located at the inside of the lens holder frame 20 and a second surface 13D which is located at the outside of the lens holder frame 20. The center of curvature of the second inner surface 13D coincides with that of the outer surface 13B of the transparent cover section 13 and is located in the inside of the capsule endoscope 10, so that the part of the transparent cover section 13 at the outside of the lens holder frame 20 does not have lens power. On the other hand, the center of curvature of the first inner surface 13C is located on the optical axis Z, outside the capsule endoscope 10, so that part of the transparent cover section 13 in the lens holder frame 20 has a positive lens power so as to function with the positive lens 13F whose center is located on the optical axis Z.

Figure 10:
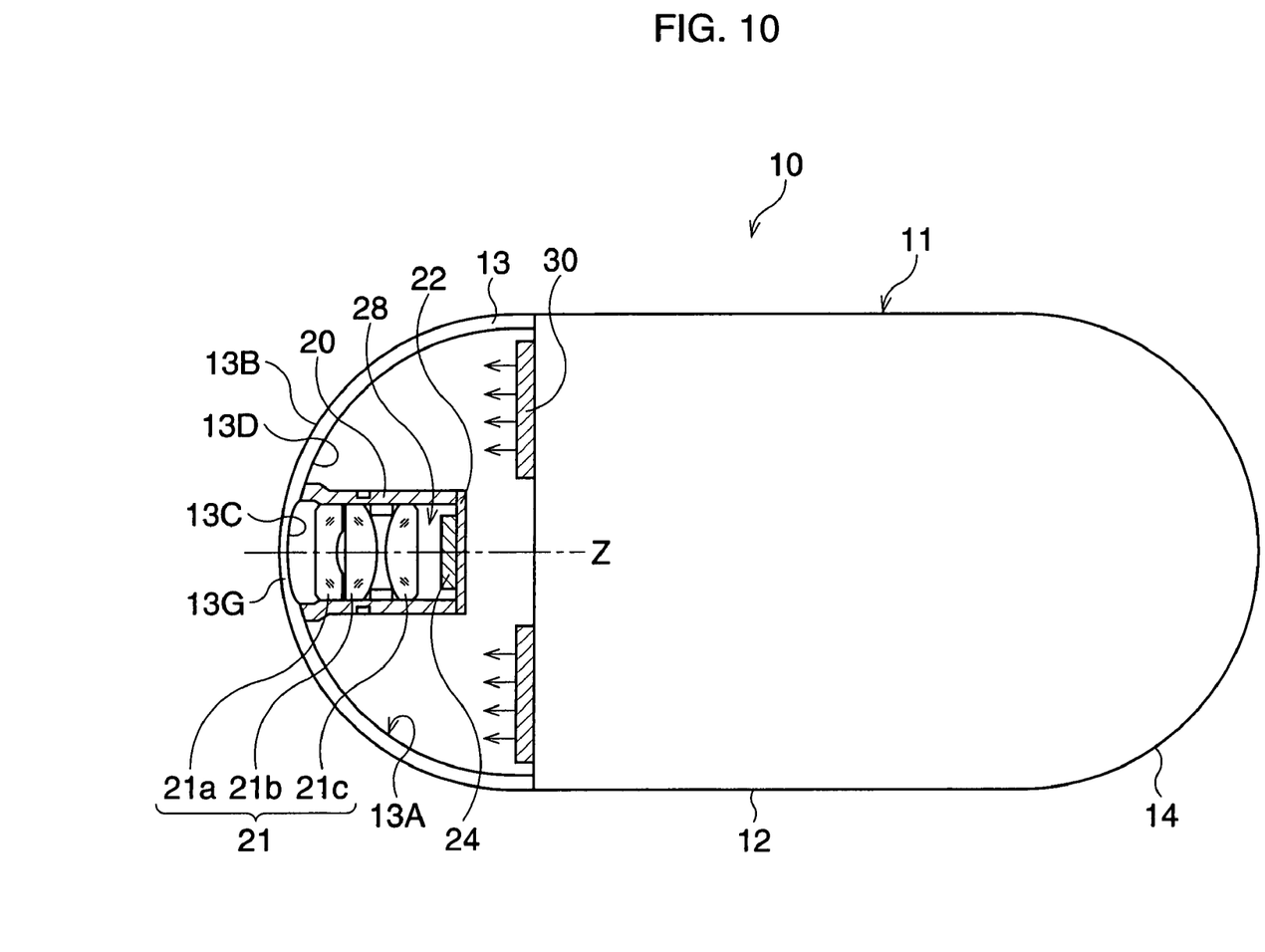
FIG. 10 is a side view, partly sectioned, of a capsule endoscope in the fifth embodiment of the present invention.

FIG. 10 shows the capsule endoscope 10 of the fifth embodiment. The difference between this embodiment and the forth embodiment is the structure of the first inner surface 13C. Next, the difference will be explained below.

In this embodiment, the inner surface 13A includes the first and second inner surfaces 13C and 13D, similar to the fourth embodiment. The second inner surface 13D has the same structure as that in the forth embodiment. On the other hand, the center of curvature of the first inner surface 13C which is located on the optical axis Z at the inside of the transparent cover section 13 is closer to the tip Y than that of the outer surface 13B. Therefore, the part of the transparent cover section 13 in the lens holder frame 20 has a negative lens power so as to function with the negative lens 13G whose center is located on the optical axis Z.

In the fourth and fifth embodiments, the transparent cover section 13 has the lens power therefore a part of the objective lens system 21 can be omitted.

Figure 11:
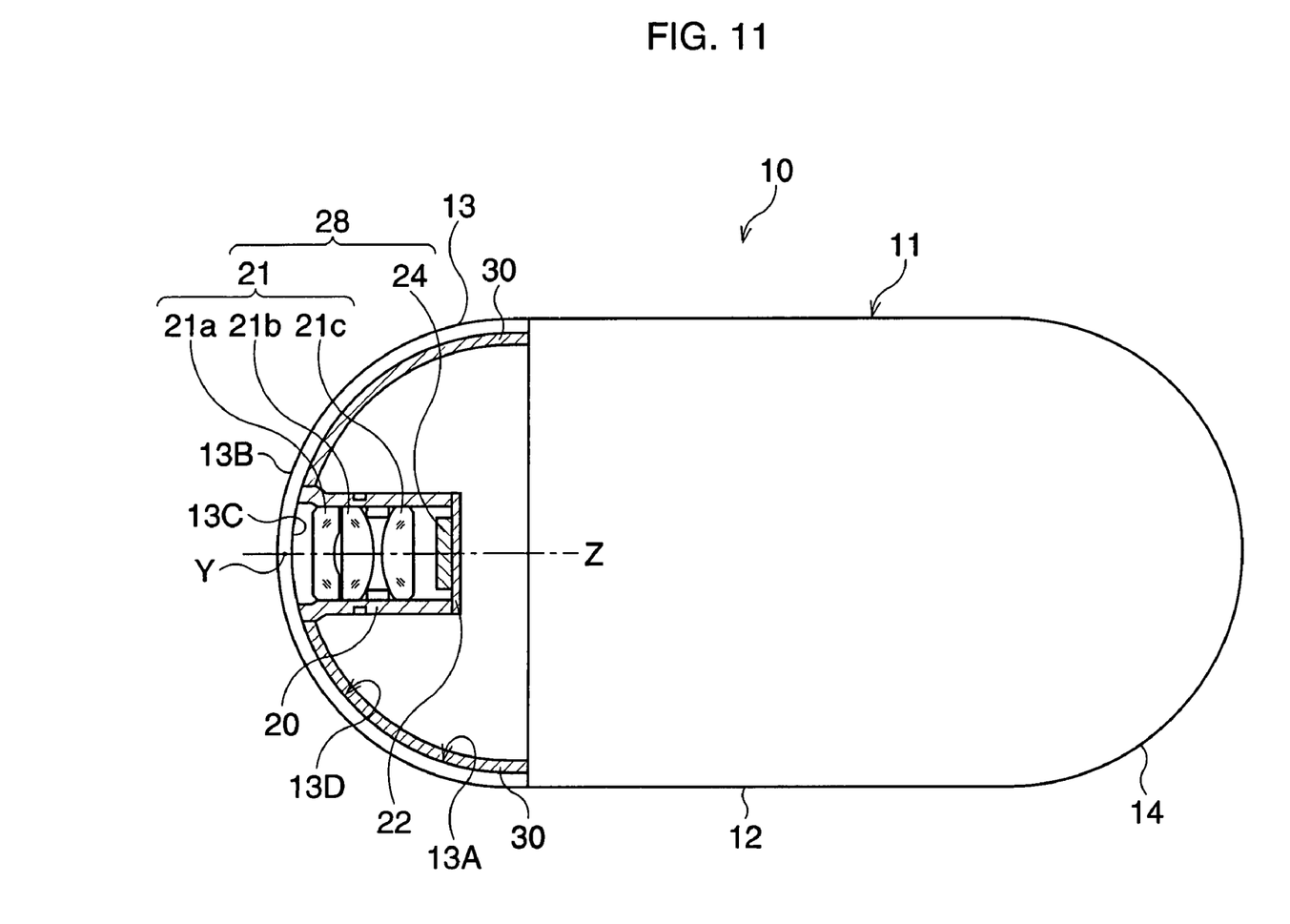
FIG. 11 is a side view, partly sectioned, of a capsule endoscope in the sixth embodiment of the present invention.
Figure 12:
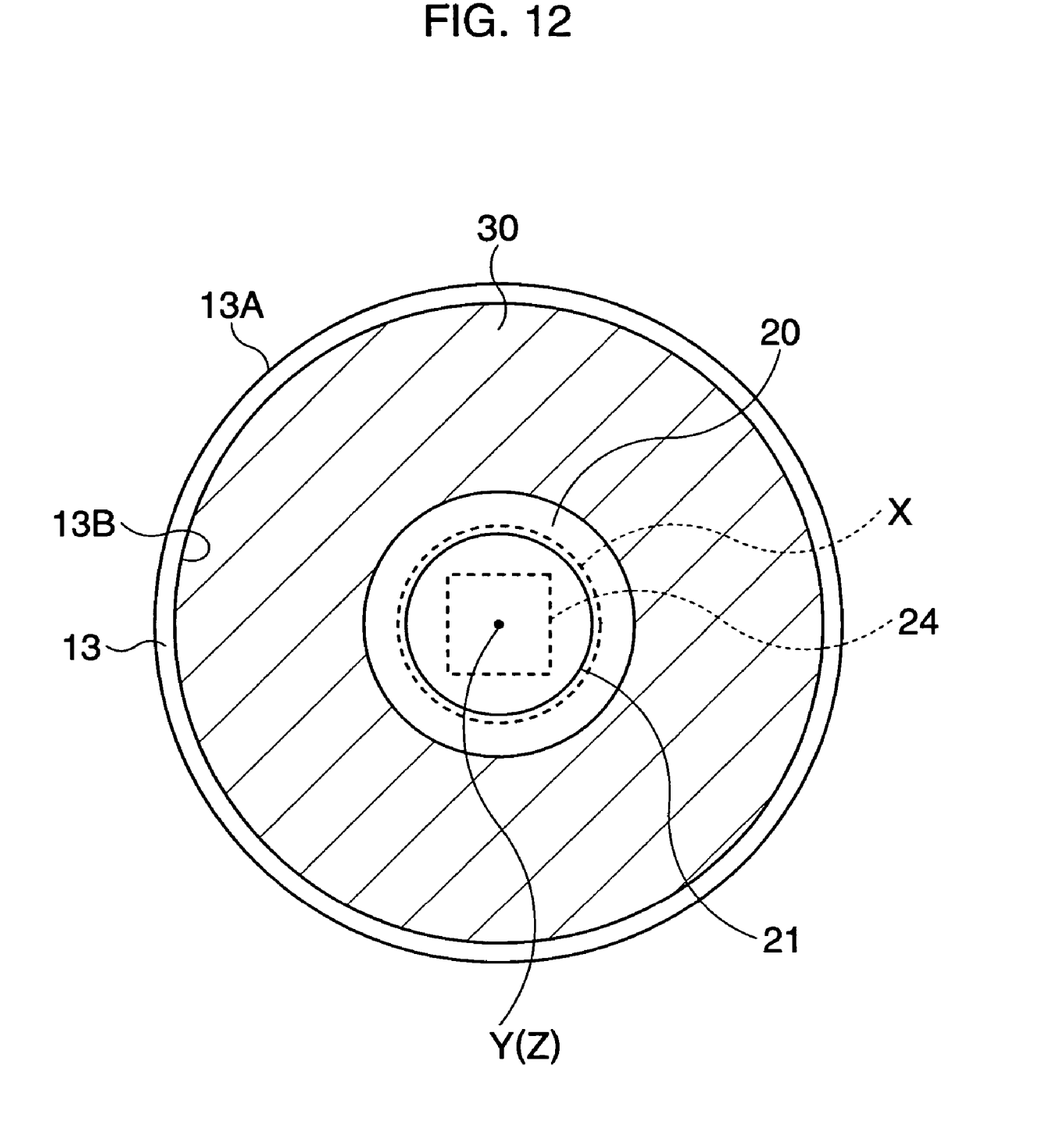
FIG. 12 is a front view of a capsule endoscope in the sixth embodiment.

FIGS. 11 and 12 show the capsule endoscope 10 of the sixth embodiment of this invention. The difference between this embodiment and the third embodiment is the position where the EL device 30 is disposed. In this embodiment, the EL device 30 is disposed in the inner surface 13A, similar to the first embodiment. Next, the difference from the third embodiment will be explained below.

The inner surface 13A includes the first and second inner surface 13C, and 13D, similar to the fourth and fifth embodiment, and the EL device 30 is disposed on the second inner surface 13D. Namely, the EL device 30 is disposed on the inner surface 13A other than that for the lens holder frame 20 and the inside thereof and extends in a ring-shape when viewed from the front as shown in FIG. 12. The structure of the EL device 30 is the same as that in the first embodiment, so this explanation is omitted.

In this embodiment, the EL device 30 is disposed on the inner surface 13A, so that almost all of the light emitted by the EL device 30 is not reflected at the transparent cover section 13, similar to the first embodiment. Therefore, the emitted light is radiated on the object effectively. Further, the emitted light which is slightly reflected by the transparent cover section 13 is not input to the photographing optical system 28, because the optical element (the negative lens 26a) which is disposed at the most forward position in the photographing optical system 28 is adjacent to the inner surface 13A and the photographing optical system 28 is enclosed in lens holder frame 20.

Further, in the first to sixth embodiments, the EL device 30 is used as the light emitting device, but other surface light emitting devices can be used as the light emitting device, for example an inorganic electroluminescent device.

Figure 13:
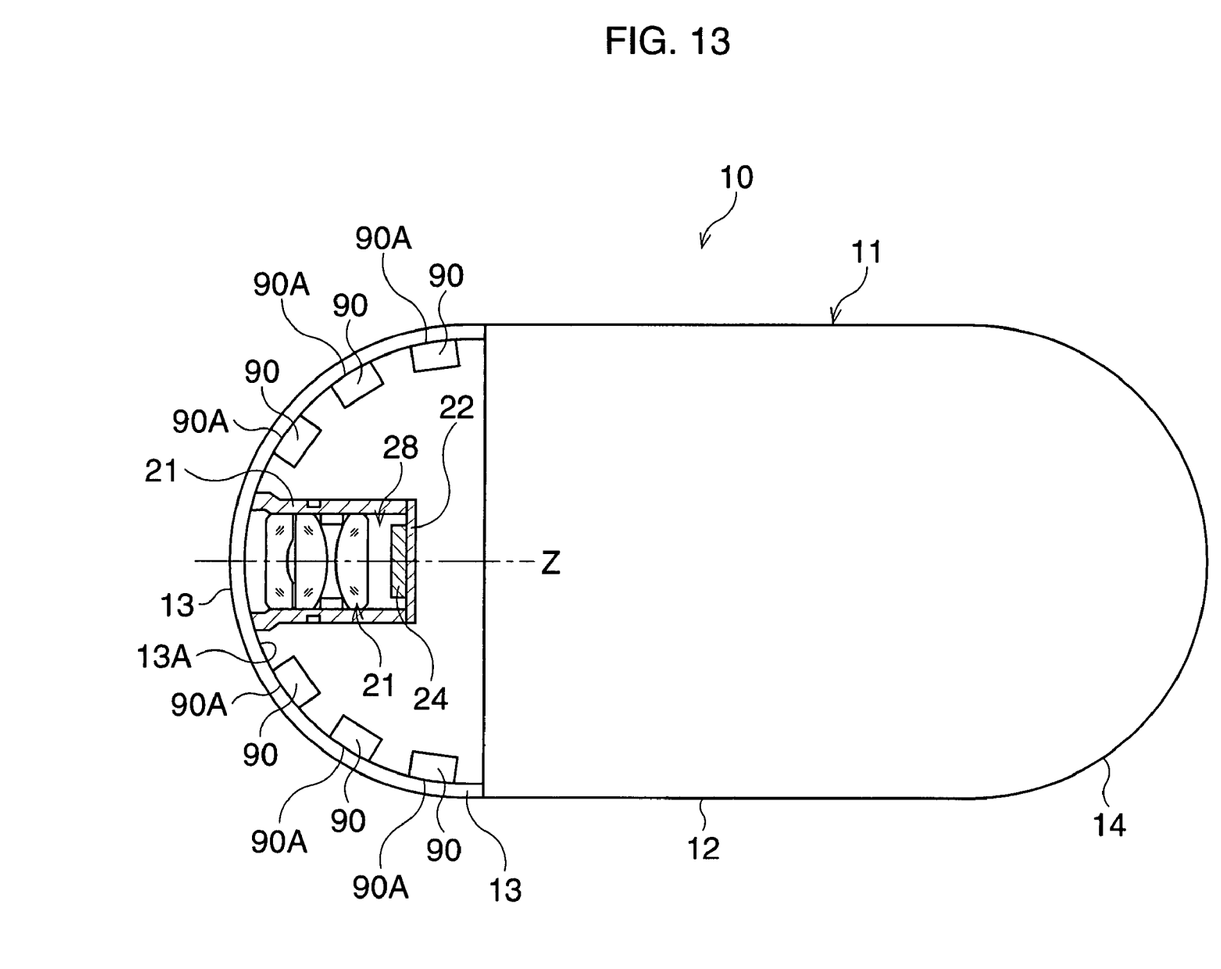
FIG. 13 is a side view, partly sectioned, of a capsule endoscope in the seventh embodiment of the present invention.

FIG. 13 shows the capsule endoscope 10 of the seventh embodiment of this invention. The difference between this embodiment and the sixth embodiment is the structure of the light emitting device. In this embodiment, inorganic LEDs are used as the light emitting device.

As shown in FIG. 13, in this embodiment, a plurality of inorganic LEDs 90 are disposed on the inner surface 13A by bonding a light emitting end 90A of each inorganic LED 90 thereto. Namely, the emitting end 90A is contacted with the inner surface 13A so that almost all of the light emitted by the inorganic LED 90 is not reflected at the transparent cover section 13, similar to the sixth embodiment.

In the first to seventh embodiments, the optical axis Z coincides with the tip Y and the center of the transparent cover section 13 (or the hemisphere portion 13t). However, the optical axis Z does not have to coincide with the tip Y and the center of the transparent cover section 13 (or the hemisphere portion 13t). Namely, the optical axis Z may incline to the line which passes through the tip Y and the center of the transparent cover section 13 (or the hemisphere portion 13t).

Although the embodiments of the present invention have been described herein with reference to the accompanying drawings, obviously many modifications and changes can be made by those skilled in this art without departing from the scope of the invention.

The present disclosure relates to subject matter contained in Japanese Patent Applications No. 2005-010137 (filed on Jan. 18, 2005) and No. 2005-078843 (filed on Mar. 18, 2005) which are expressly incorporated herein, by references, in their entirety.

The invention claimed is:

1. A capsule endoscope, comprising:
an outer cover that seals an inside space of said capsule endoscope, said outer cover including a transparent cover having a dome-shape;
a surface light emitting device that is disposed in said inside space, such that light is emitted to an object through said transparent cover, said surface light emitting device comprising a layer extending along an inner surface of said dome-shape of said transparent cover, wherein said surface light emitting device directly contacts said inner surface of said dome-shape, and wherein a surface of said surface light emitting device is laminated on said inner surface of said dome-shape; and
a photographing optical system that is disposed opposite to said transparent cover in said inside space, capturing light reflected from said object, which passes through said transparent cover.

2. The capsule endoscope according to claim 1, wherein said transparent cover comprises a hemispherical portion.

3. The capsule endoscope according to claim 1, wherein said surface light emitting device extends along substantially an entire inner surface of said transparent cover excluding a circumferential portion surrounding a tip of said transparent cover.

4. The capsule endoscope according to claim 1, wherein said surface light emitting device is disposed on substantially an entire inner surface of said transparent cover excluding a field of vision of said photographing optical system.

5. The capsule endoscope according to claim 1, wherein said surface light emitting device is an organic electroluminescent device.

6. The capsule endoscope according to claim 1, wherein said inner surface of said dome-shape comprises a cylindrical portion and a hemispherical portion, and said surface light emitting device is provided on said cylindrical and hemispherical portions.

\* \* \* \* \*